(12) United States Patent
Kim et al.

(10) Patent No.: US 10,066,514 B2
(45) Date of Patent: Sep. 4, 2018

(54) METHOD OF RECYCLING ENERGY IN PROCESS OF BUTADIENE PREPARATION

(71) Applicant: LG CHEM, LTD., Seoul (KR)

(72) Inventors: Mi Kyung Kim, Daejeon (KR); Jeong Seok Lee, Daejeon (KR); Jae Ik Lee, Daejeon (KR); Dae Hyeon Kim, Daejeon (KR); Jong Ku Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 87 days.

(21) Appl. No.: 15/108,519

(22) PCT Filed: Jul. 2, 2015

(86) PCT No.: PCT/KR2015/006816
§ 371 (c)(1),
(2) Date: Jun. 27, 2016

(87) PCT Pub. No.: WO2016/003215
PCT Pub. Date: Jan. 7, 2016

(65) Prior Publication Data
US 2016/0319704 A1    Nov. 3, 2016

(30) Foreign Application Priority Data

Jul. 2, 2014   (KR) .......................... 10-2014-0082674

(51) Int. Cl.
*F01K 25/14*    (2006.01)
*F01K 7/16*    (2006.01)
(Continued)

(52) U.S. Cl.
CPC ............... *F01K 25/14* (2013.01); *C07C 5/48* (2013.01); *C07C 7/00* (2013.01); *C07C 7/04* (2013.01);
(Continued)

(58) Field of Classification Search
CPC ... F01K 25/14; F01K 5/00; F01K 7/16; C07C 5/48; C07C 7/04; C07C 7/00;
(Continued)

(56) References Cited

U.S. PATENT DOCUMENTS 4,568,364 A * 2/1986 Galstaun ................ B01D 53/14
95/176
5,192,486 A * 3/1993 Whipp ................ C21B 13/0033
266/156

(Continued)

FOREIGN PATENT DOCUMENTS

CN    102442874 A    5/2012
CN    102675027 A    9/2012
(Continued)

*Primary Examiner* — Hoang Nguyen
(74) *Attorney, Agent, or Firm* — Dentons US LLP

(57) ABSTRACT

Provided is a method for recycling energy in process of butadiene preparation, which includes, in the process of preparing butadiene using oxidative dehydrogenation reaction, steps of: a) supplying part or all of a light gas discharged from a solvent absorption tower to a turbine to produce electricity; b) passing the light gas passed through the turbine through one or more device units provided with a heat exchanger; and c) feeding the light gas passed through the device units provided with the heat exchanger into a reactor, according to which more economical butadiene preparation process is provided, by reducing net energy value required in process of butadiene preparation using oxidative dehydrogenation reaction.

10 Claims, 3 Drawing Sheets

(51) Int. Cl.
*C07C 5/48* (2006.01)
*C07C 7/00* (2006.01)
*C07C 7/04* (2006.01)
*H02N 11/00* (2006.01)
*F01D 15/10* (2006.01)
*F01D 25/08* (2006.01)
*F01K 5/00* (2006.01)

(52) U.S. Cl.
CPC .............. *F01D 15/10* (2013.01); *F01D 25/08* (2013.01); *F01K 5/00* (2013.01); *F01K 7/16* (2013.01); *H02N 11/00* (2013.01); *F05D 2260/213* (2013.01)

(58) Field of Classification Search
CPC ......... F01D 15/10; F01D 25/08; H02N 11/00; F05D 2260/213
USPC .................................... 60/645, 670
See application file for complete search history.

(56) References Cited

U.S. PATENT DOCUMENTS

| | | | | |
|---|---|---|---|---|
| 5,948,378 A | * | 9/1999 | Koveal | C01B 3/58 252/373 |
| 8,062,408 B2 | * | 11/2011 | Chen | B01D 53/1425 95/163 |
| 8,397,509 B2 | * | 3/2013 | Hwang | F02C 1/005 60/39.182 |
| 2008/0119680 A1 | | 5/2008 | Crone et al. | |
| 2008/0183024 A1 | | 7/2008 | Klanner et al. | |
| 2014/0163292 A1 | | 6/2014 | Grüne et al. | |
| 2014/0200381 A1 | | 7/2014 | Josch et al. | |

FOREIGN PATENT DOCUMENTS

| | | |
|---|---|---|
| DE | 102005002127 | 7/2006 |
| JP | S59164730 | 9/1984 |
| JP | S62143808 | 6/1987 |
| JP | 2010090082 | 4/2010 |
| JP | 2010090083 | 4/2010 |
| JP | 2011251220 | 12/2011 |
| JP | 2012500713 | 1/2012 |
| JP | 2012077076 | 4/2012 |
| KR | 10-2013-0036467 | 4/2013 |
| WO | 2013-148908 A1 | 10/2013 |
| WO | 103657536 A | 3/2014 |
| WO | 103965001 A | 8/2014 |

* cited by examiner

METHOD OF RECYCLING ENERGY IN PROCESS OF BUTADIENE PREPARATION

CROSS-REFERENCE TO RELATED APPLICATIONS

This application is a National Stage Entry of International Application No. PCT/KR2015/006816, filed on Jul. 2, 2015, and claims the benefit of and priority to Korean Application No. 10-2014-0082674, filed on Jul. 2, 2014, all of which are hereby incorporated by reference in their entirety for all purposes as if fully set forth herein.

TECHNICAL FIELD

The present disclosure relates to a method of recycling energy in process of butadiene preparation.

BACKGROUND ART

Butadiene is an important basic chemical, is used as an intermediate for a variety of petrochemicals including synthetic rubbers or electronic materials, and is currently one of the most important feedstock in the petrochemical market for which demand and values keep increasing. Methods of butadiene preparation may involve reactions such as naphtha cracking, n– butene direct dehydrogenation, n-butene oxidative dehydrogenation, etc.

Among these, the butadiene preparation method using oxidative dehydrogenation involves reaction at high temperatures ranging from 300 to 600° C., and the butadiene prepared from such reaction is dissolved in the absorption solvent, from which light gas is separated. After the solvent is removed and distilled, high purity butadiene is obtained. Meanwhile, of the separated light gas, components effective to the reaction are circulated and re-introduced into the reactor, while the rest is discharged out of the system along with purge stream.

DISCLOSURE

Technical Problem

During butadiene preparation by the oxidative dehydrogenation reaction, the light gas discharged from an upper end of a solvent absorption tower, which is the high pressure gas, may be partially circulated back into the reactor.

The present disclosure proposes to produce electricity by driving a turbine with a high pressure gas discharged from an upper end of the solvent absorption tower, and at the same time, to directly produce refrigerant using a stream of light gas which is decreased in temperature as it is passed through the turbine, or to reduce refrigerant by exchanging heat with the individual device in process.

Technical Solution

In an exemplary embodiment to achieve the objects of the present disclosure, a method of recycling energy in process of butadiene preparation using oxidative dehydrogenation reaction is provided, which includes steps of: a) supplying part or all of a light gas discharged from a solvent absorption tower to a turbine to produce electricity; b) passing the light gas passed through the turbine through one or more device units provided with a heat exchanger; and c) introducing the light gas passed through the device units provided with the heat exchanger into a reactor.

Advantageous Effects

According to the present disclosure, it is possible to produce electricity by driving a turbine with a high pressure gas discharged from an upper end of the solvent absorption tower, and at the same time, to directly produce refrigerant using a stream of light gas which is decreased in temperature as it is passed through the turbine, or to reduce refrigerant by exchanging heat with the individual device in process.

As a result, more economical butadiene preparation process is provided.

MODE FOR INVENTION

Hereinbelow, preferred exemplary embodiments of the present disclosure will be described with reference to the accompanying drawings. Although the present disclosure is described with reference to certain exemplary embodiments, these are provided merely for exemplary purpose, and the technical concept and core configuration and operation of the present disclosure are not limited thereto. In particular, the term "light gas" which is used throughout the description including the claims and the abstract should be understood as referring to a gaseous component which includes nitrogen, oxygen, steam, carbon monoxide, or carbon dioxide among the reaction products produced in the oxidative dehydrogenation reaction. Further, the term "effective component" as used herein should be understood as referring to a component which is effective to a butadiene preparation reaction, such as nitrogen, oxygen, unreacted material or butadiene.

Apparatus for Preparing Butadiene

Figure 1:
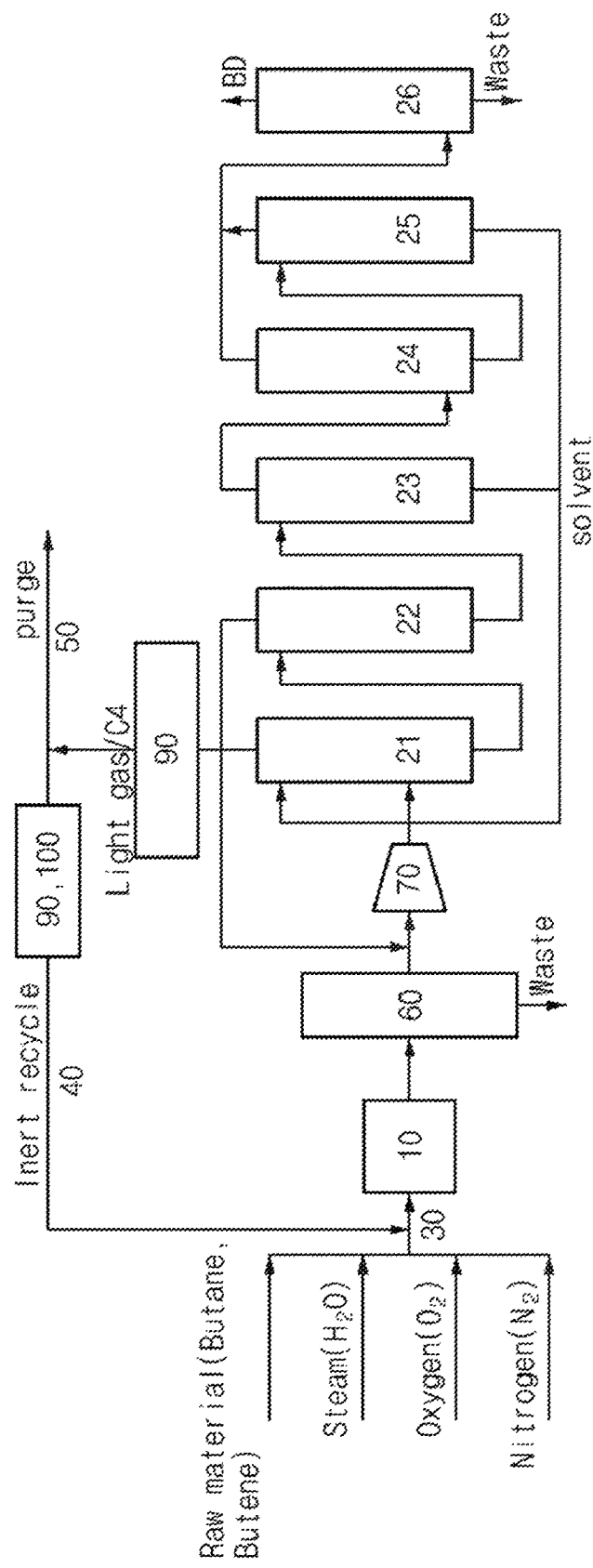
FIG. 1 schematically illustrates a process of preparing butadiene using oxidative dehydrogenation reaction according to an exemplary embodiment.

An apparatus for preparing butadiene, which is to implement a method for preparing butadiene by way of the oxidative dehydrogenation reaction as described above, may include individual pipelines to feed respective components of a first stream 30 including $C_4$ fraction, steam, oxygen $O_2$ and nitrogen $N_2$, into a reactor 10, or include a plurality of individual pipelines which are branched off from one single pipeline which is directly connected to the reactor 10 and to which the components included in the first stream are individually fed (see FIG. 1).

Further, the apparatus includes the reactor 10 which is connected with the pipelines and in which the oxidative dehydrogenation reaction occurs. A mixer may be additionally included, provided on a front end of the reactor to mix the components included in the first stream before being fed into the reactor (see FIG. 1).

Further, a gas separator may be additionally included, which includes at least one of a solvent absorption tower 21 and an air stripper tower 22 to separate the light gas from the $C_4$ mixture containing butadiene obtained from the reactor 10 (see FIG. 1).

Further, for refining purposes to obtain high purity butadiene, refining devices may be provided, such as a solvent separator/recoverer including a solvent recovery tower 23, a high boiling removal tower 24, and a solvent refining tower 25, and a butadiene refining tower 26 to refine the obtained butadiene to high purity (see FIG. 1).

Meanwhile, the apparatus for preparing butadiene according to an exemplary embodiment may additionally include an inert recycle line which allows a second stream 40 including one or more of nitrogen $N_2$ and carbon dioxide $CO_2$ of the light gas separated at the gas separator to be re-introduced into the reactor, and a discharge line to discharge a third stream 50 including purge out of the system (see FIG. 1).

Further, a quencher including a quenching tower 60 provided between the gas separator and the reactor to quench the reaction product obtained from the reactor, a compressor 70 for compressing the reaction product, and a dehydrator for removing water from the reaction product, may be additionally included.

Meanwhile, a turbine 90 may be connected to the discharge line through which the light gas from the upper end (top) of the solvent absorption tower is discharged. The turbine is provided to produce electricity (see FIG. 1).

The turbine 90 may use, without limitation, conventionally known ones. For example, the turbine may use an impulse turbine or a reaction turbine, or may use any one selected from a condensing turbine, back pressure turbine, and an extraction turbine, depending on state the steam is used.

Process for Preparing Butadiene

First, the first stream including $C_4$ fraction, steam, oxygen $O_2$ and nitrogen $N_2$ is introduced into the reactor and undergoes oxidative dehydrogenation reaction.

The $C_4$ fraction may refer to $C_4$ raffinate-1, 2, 3 remaining after separation of useful compounds from the $C_4$ mixture produced from the naphtha cracking, and may also refer to $C_4$ group which can be obtained through ethylene dimerization. According to an exemplary embodiment, the $C_4$ fraction may be a mixture of one or two or more selected from the group consisting of n-butene, trans-2-butene, cis-2-butene and 1-butene.

In the oxidative dehydrogenation reaction, the steam or nitrogen N2 is the diluent gas which is introduced to reduce risk of explosion of a reactant, and also to prevent catalyst from coking and to remove heat of reaction.

Meanwhile, the oxygen $O_2$ is an oxidant which reacts with $C_4$ fraction to cause dehydrogenation.

According to an exemplary embodiment, the first stream 30 may refer to a stream of $C_4$ fraction, steam, oxygen $O_2$ and nitrogen $N_2$ which are introduced into the reactor through the respective individual pipelines.

Meanwhile, in another exemplary embodiment, the first stream 30 may refer to a mixed stream of $C_4$ fraction, steam, oxygen $O_2$ and nitrogen $N_2$, which is introduced into the reactor after the components contained therein are passed through a plurality of pipelines branched off from one single pipeline directly connected to the reactor to allow individual feeding of the components therethrough and then mixed in the one single pipeline or mixed by a mixer located at a front end of the reactor.

According to an exemplary embodiment, the $C_4$ fraction, steam, oxygen and nitrogen contained into the first stream may be introduced in the pipeline in gaseous state, in which the gas may be previously heated to a temperature advantageous for oxidative dehydrogenation reaction before being introduced.

According to an exemplary embodiment, the catalyst charged into the reactor is not limited to any specific example, provided that the catalyst causes $C_4$ fraction to undergo oxidative dehydrogenation reaction to produce butadiene. For example, the catalyst may be ferritic catalyst or bismuth molybdate-based catalyst.

According to an exemplary embodiment, the catalyst may be bismuth molybdate-based catalyst, and the bismuth molybdate-based catalyst may include one or more selected from the group consisting of bismuth, molybdenum and cobalt. Further, the bismuth molybdate-based catalyst may be multicomponent bismuth molybdate-based catalyst. Note that the type and amount of the reaction catalyst may vary depending on specific conditions.

According to an exemplary embodiment, the reactor 10 is not particularly limited, as long as oxidative dehydrogenation reaction is allowed to occur therein. For example, the reactor 10 may be a tubular reactor, a tank reactor or a fluidized bed reactor. In another example, the reactor may be a fixed bed reactor, a multitubular fixed bed reactor or a plate reactor.

As described above, oxidative dehydrogenation reaction occurs as the first stream 30 including $C_4$ fraction, steam, oxygen $O_2$ and nitrogen $N_2$ is introduced into the reactor 10 charged with the catalyst. The oxidative dehydrogenation reaction is the exothermic reaction with the main reaction formula as formula 1 or 2 below.

$$C_4H_8 + \tfrac{1}{2}O_2 C_4H_6 + H_2O \qquad \text{[Reaction Formula 1]}$$

$$C_4H_{10} + O_2 C_4H_6 + 2H_2O \qquad \text{[Reaction Formula 2]}$$

Butadiene is produced, as the hydrogen of butane or butene is removed in the oxidative dehydrogenation reaction. Meanwhile, the oxidative dehydrogenation reaction is accompanied with side reaction in addition to the major reaction as expressed by the above chemical formula 1 or 2, according to which a side reaction product including a low-boiling and aqueous by-product such as carbon monoxide CO, carbon dioxide $CO_2$, acetylene or carbonyl group, and a high-boiling by-product such as phenol and coumarin may be produced. The side reaction product has to be separated and discharged out of the system to ensure that it is not continuously accumulated in process.

Meanwhile, the $C_4$ mixture containing butadiene obtained from the reactor may additionally undergo post treatment so that high purity butadiene is obtained. The post treatment may include one or more steps selected from the group consisting of quenching step using at least a plurality of quenching towers, compressing step using a compressor, dehydrating step using a dehydrator, a gas separating step using a gas separator, and refining step using a solvent separator/recoverer and a refining tower.

Quenching Step

According to an exemplary embodiment, the reaction product obtained from the reactor may undergo quenching step.

The reaction product obtained from the reactor may be in high temperature gas form, in which case it has to be cooled before being fed into the gas separator.

The quenching method for use in the quenching step is not limited to any specific example. For example, the quenching step may use a method of directly contacting the cooling solvent with the reaction product, or a method of indirectly contacting the cooling solvent with the reaction product.

Dehydrating Step

According to an exemplary embodiment, dehydrating step may be additionally included, which removes water from the reaction product obtained from the reactor.

When the water remains in the reaction product, this can cause equipment to be corroded in the following stages such as solvent absorption, separation and refinement, or cause impurities to be accumulated in the solvent. Accordingly, the water has to be removed.

The dehydrating method for use in the dehydrating step is not limited to any specific example. For example, dehydrating means for use in the dehydrating step may be a drier (i.e., water absorber) such as calcium oxide, calcium chloride, or molecular sieve, although exemplary embodiments are not limited thereto. Among the examples of the dehydrating means mentioned above, the molecular sieve may be advantageous in view of ease of regeneration, ease of handling, and so on.

Gas Separating Step

According to an exemplary embodiment, the reaction product obtained from the reactor is contacted with the absorption solvent at the solvent absorption tower during which only the $C_4$ mixture containing butadiene is selectively absorbed into the absorption solvent, while the rest (i.e., light gas) is separated and removed.

Specifically, as the reaction product obtained from the reactor is contacted with the absorption solvent in counter-current contact, the $C_4$ mixture containing butadiene is selectively absorbed into the absorption solvent, while the remaining light gas is passed through the top of the absorption tower and exited through the pipeline.

The absorption tower may be, for example, a packed tower, a wetted-wall tower, a spray tower, a cyclone scrubber, a bubble tower, a bubble agitation tank, a plate tower (bubble cap tower, perforated plate tower) or a foam separating tower, but not limited thereto.

The absorption solvent may use any of already known absorption solvent in the art, such as $C_6$ to $C_{10}$ saturated hydrocarbon, $C_6$ to $C_8$ aromatic hydrocarbon, or amide compound, for example.

Further, the absorption solvent may be a mixture of one or more, or two or more selected from the group consisting of dimethylformamide (DMF), methylpyrrolidone (NMP), acetonitrile (ACN), dimethylacetamide (DMA), dimethyl sulfoxide (DMSO), acetonitrile (ACN), vinylcyclohexane, toluene, benzene, xylene, styrene, octane, octene, ethylcyclohexene, nonane, nonene and furfural.

Meanwhile, according to an exemplary embodiment, the light gas discharged through the top of the absorption tower and the pipeline is divided into the second stream 40 and the third stream 50 (see FIG. 1).

The second stream may be a concentrated stream containing one or more selected from the group consisting of nitrogen and carbon dioxide, and it is circulated along the inert recycle line and re-introduced into the reactor. The second stream may additionally include unreacted material and butadiene in addition to nitrogen $N_2$ and carbon dioxide $CO_2$, in which case the carbon dioxide contained in the second stream may be re-introduced through the inert recycling into the reactor and act as a mild oxidant or a diluent gas for the oxidative dehydrogenation reaction in the reactor.

Meanwhile, the third stream is a purge stream and it is discharged out of the system through a discharge line separate from the second stream. The third stream may also additionally include nitrogen $N_2$, carbon dioxide $CO_2$, unreacted material, and/or butadiene.

Meanwhile, according to an exemplary embodiment, the absorption solvent may be used to selectively absorb only the $C_4$ mixture containing butadiene, but it may also dissolve some gases such as nitrogen, carbon dioxide, etc. Accordingly, air stripping step may be additionally performed to remove gases such as nitrogen or carbon dioxide, and such air stripping step may be performed in an air stripper tower.

The air stripping method for the air stripping step is not limited to any specific example only, but may be the generally known method in the related art.

Figure 3:
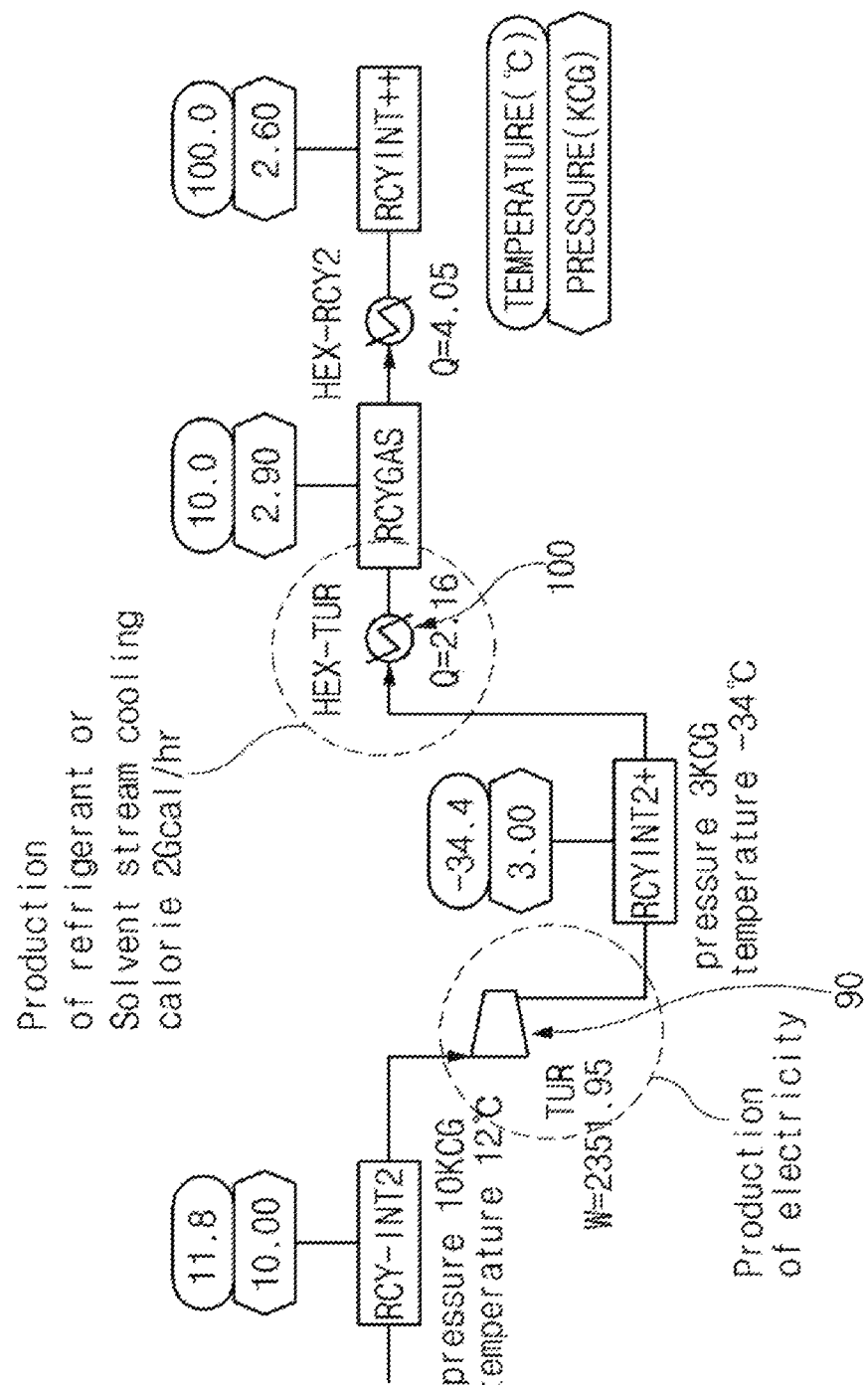
FIG. 3 schematically illustrates a process of producing electricity by using high pressure gas separated at a gas separating step, while also producing refrigerant by using a stream of light gas which is decreased in temperature, or cooling the solvent stream, according to an exemplary embodiment.

Meanwhile, the high pressure light gas separated from the top of the solvent absorption tower and through the pipeline, may pass through the turbine 90 connected with the pipeline (see FIGS. 1 and 3). The turbine is an apparatus provided to produce electricity using the high pressure light gas as introduced.

Refining Step

According to an exemplary embodiment, the $C_4$ mixture containing butadiene included in the absorption solvent undergoes refining step to be produced into high purity butadiene. The refining step may include one or more selected from a solvent separator/recoverer including the solvent recovery tower 23 to separate and recover absorption solvent, a high boiling point removal tower 24 to remove high boiling component, and a solvent refining tower 25, and the butadiene refining tower 26 to refine high purity butadiene (see FIG. 1).

According to an exemplary embodiment, the method for separating and recovering solvent may be a distillation method, although exemplary embodiments are not limited to any specific example only. According to the distillation method, the distillation process begins, as the absorption solvent with the $C_4$ mixture containing butadiene dissolved therein is supplied to the solvent recovery tower, by the reboiler and the condenser. After the distillation process, the $C_4$ mixture containing butadiene is extracted near the top of the tower.

The absorption solvent separated by the process described above is extracted from a bottom of the solvent recovery tower, and the extracted absorption solvent may be recycled to the previous processes and used. Some of the absorption solvent may be extracted before recycle and undergo impurity removal process with the known refining method, such as, distillation, decantation, sedimentation, and/or contact with absorbent or ion exchange resin, for the possible impurities that may be contained in the absorption solvent.

According to an exemplary embodiment, the $C_4$ mixture containing butadiene separated from the absorption solvent may be fed to the high boiling removal tower for separation of the high boiling components.

The process at the high boiling removal tower involves removing a high boiling component (i.e., a component with a higher solubility than butadiene), during which the component with higher solubility than butadiene dissolves in the solvent. The solvent may be discharged from the bottom of the tower and conveyed to the solvent refining tower.

Meanwhile, after removal of the high boiling component, the butadiene may be discharged from the top of the high boiling removal tower and conveyed to the butadiene refining tower. According to an exemplary embodiment, the high boiling/low boiling components are removed while the butadiene conveyed to the refining tower goes through the refining tower, thus leaving high purity butadiene.

According to an exemplary embodiment, the resulting butadiene that can be obtained after undergoing the set of steps described above has from 99.0 to 99.9% purity.

Meanwhile, the high temperature absorption solvent recovered in the butadiene preparation process described above may be recycled, and the heat generated from the cooling of the high temperature absorption solvent for recycle thereof may be utilized to reduce the net energy value necessary in process of butadiene preparation.

Method of Recycling Energy in Process of Butadiene Preparation

Figure 2:
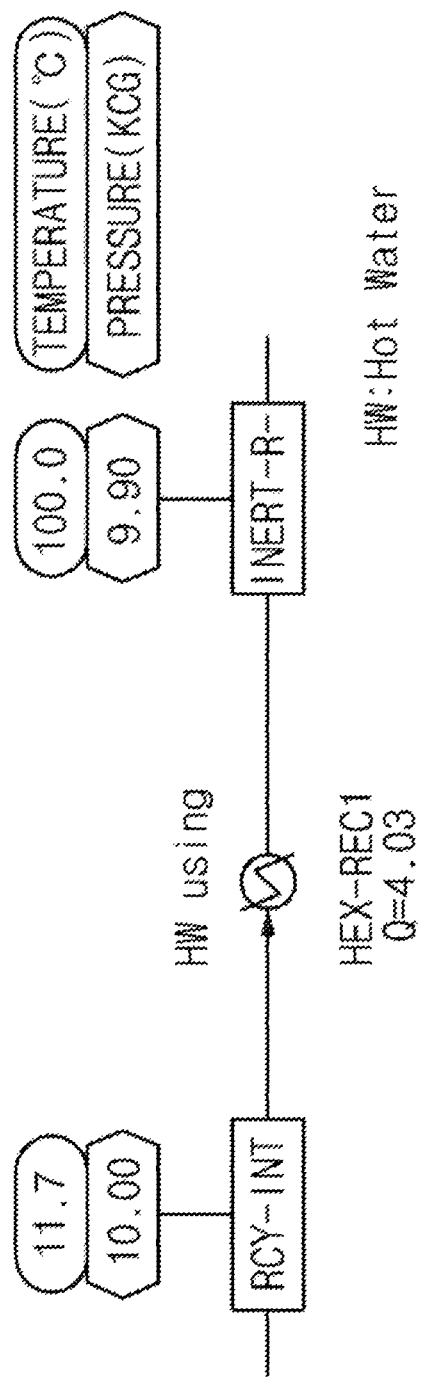
FIG. 2 schematically illustrates a process of re-circulating and feeding light gas separated at a gas separating step into a reactor, according to a related technology.

Referring to FIGS. 1 and 2, in related technology, the gas discharged from the top (upper end) of the solvent absorption tower 21 is divided at a gas separating step into the second stream 40 and the third stream 50. The light gas (temperature 11.7° C., pressure 10.00 KCG) of the second stream 40 undergoes the process of heating with hot water (HW) and re-circulating and re-introducing into the reactor 10 (in an atmosphere of temperature 100° C., pressure 9.90 KCG).

According to an exemplary embodiment, a method of recycling energy in process of butadiene preparation using oxidative dehydrogenation reaction is provided, which includes steps of: a) supplying part or all of a light gas discharged from a solvent absorption tower to a turbine to produce electricity; b) passing the light gas passed through the turbine through one or more device units provided with a heat exchanger; and c) introducing the light gas passed through the device units provided with the heat exchanger into a reactor.

First, high pressure light gas is discharged through the pipeline connected to the upper end (top) of the solvent absorption tower, and the light gas discharged through such pipeline is fed to the turbine connected to the pipeline (step a).

The high pressure light gas may be supplied to the turbine to rotate the turbine and produce electricity, and the high pressure light gas may have pressure ranging from 5 to 20 KCG. Meanwhile, the pressure of the light gas discharged from the turbine after producing electricity at the turbine may range from 1 to 5 KCG.

Further, according to an exemplary embodiment, the temperature of the light gas supplied to the turbine may range from 5 to 50° C., and the temperature of the light gas discharged from the turbine after producing electricity at the turbine may range from −50 to 20° C., or the temperature of the light gas discharged from the turbine ranges from −50 to 0° C.

Meanwhile, according to an exemplary embodiment, the turbine may provide electricity yield ranging from 1 to 200 kWh/BD ton.

Next, the light gas discharged from the turbine may be conveyed to one or more device units equipped with heat exchangers where refrigerants may be produced from the device unit, or alternatively, fluid stream may be directly cooled (step b).

The heat exchanger is not limited to any specific example, as long as it causes transfer of heat between high temperature fluid and low temperature fluid. For example, the heat exchanger may be a pressure vessel form.

According to an exemplary embodiment, the heat exchanger may be configured as a vessel which is partitioned into two sides so that the high temperature fluid is introduced into one side and the low temperature fluid is introduced into the other side, thus allowing heat to transfer from the high temperature fluid to the low temperature fluid. As a result, the high temperature fluid is in cooler state than its original state when discharged, while the low temperature fluid is in heated state than its original state when discharged.

The heat exchanger may be a multistage heat exchanger in which same types of heat exchangers are sequentially connected in series.

Meanwhile, an individual in-process device unit according to the present disclosure may refer to one or more selected from a heat exchanger and a solvent streamline. Each of the individual device unit may be provided with a heat exchanger.

According to an exemplary embodiment, the device unit may be a heat exchanger, and the fluid circulating the heat exchanger may be water.

The light gas discharged from the turbine is at a relatively low temperature and it cools down the fluid circulating the heat exchanger by heat transfer, as it passes through the heat exchanger. Accordingly, the fluid circulating the heat exchanger can be utilized as a refrigerant afterward. After the fluid passes through the heat exchanger, the temperature of the fluid may range from −10 to 30° C., for example.

According to yet another exemplary embodiment, the device unit may refer to a solvent streamline equipped with a heat exchanger. The solvent streamline may be a line through which the high temperature solvent stream, which is recovered from one or more device units selected from the solvent recovery tower and the solvent refining tower, is fed to the absorption tower, and the solvent stream is a liquid which is at a relatively high temperature and it has to go through cooling step before being fed into the absorption tower. As such, the relatively low temperature light gas, which is discharged from the turbine, cools down the relatively high temperature solvent stream by heat transfer when contacting the solvent streamline. The cooling described above may cool down the temperature of the solvent stream in the solvent streamline to a range from 5 to 50° C., for example.

After going through the steps described above, part of the light gas may be circulated and re-introduced into the reactor (second stream) (step c). Meanwhile, the rest of the light gas is entrained in the purge and discharged out of the system (third stream).

Hereinbelow, certain exemplary embodiments will be described in more detail with reference to the accompanying drawings. However, one with ordinary knowledge in the related art will be readily able to understand that these exemplary embodiments are provided only for illustrative purpose and that the scope of the present disclosure is not limited to any of the detailed description of the exemplary embodiment.

Referring to FIG. 1, the butadiene preparation process may include the solvent absorption tower 21 to separate the $C_4$ mixture containing butadiene obtained from the reactor 10, from the light gas. That is, the light gas is discharged through the pipeline connected to an upper end of the solvent absorption tower 21.

The light gas discharged from the upper end of the solvent absorption tower 21 may be fed back into the reactor 10, after undergoing heat exchange with the hot water (HW). More specifically, referring to FIG. 2, the light gas at temperature 11.7° C. and pressure 10.00 KGC may go through heat exchange with the hot water, and after the heat exchange, the light gas, now at temperature 100.0° C. and pressure 9.90 KGC, may be fed back to the reactor 10.

Further, FIG. 3 is a flowchart that expresses a set of processes illustrated in FIG. 2 in more details, in which the processes, including electricity production, and generation of refrigerant by way of energy exchange, are schematically illustrated. Referring to FIG. 3, the light gas (11.8° C., 10.00 KGC) discharged from the upper end of the solvent absorption tower 21 may be fed to the turbine, thus operating the turbine and producing electricity. After passing through the turbine, the light gas (−34.4° C., 2.90 KCG) may produce approximately 92 kWh/BD ton of electricity, after which the light gas may be fed to the heat exchanger and used as the refrigerant. The calories of 0.09 Gcal/BD ton may be needed to heat the light gas (−34.4° C., 2.90 KCG) to about 10° C., and it is possible to directly produce the refrigerant or cool down the absorption solvent with this calories. The light gas (10.0° C., 2.90 KCG) discharged from the heat exchanger may then be set to temperature 100.0° C. and pressure 2.60 KGC by being heated with the hot water, and then fed back into the reactor.

According to exemplary embodiments of the present disclosure described above, the method for recycling energy in process of butadiene preparation rotates the turbine with the low-temperature, high-pressure light gas separated in the gas separating step, thus producing electricity, and at the same time, it either produces refrigerant with the light gas which is naturally decreased to a relatively low temperature while passing through the turbine, or decreases the temperature of the fluid stream included in the fluid streamline. Accordingly, the net energy value required for the process can be reduced, which in turn can improve economy of the butadiene preparation process. Additionally, efficient operation of the process can be provided, since the condition is set as high-temperature and low-pressure condition which is suitable for feeding back into the reactor.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

Description of Reference Numerals

| | |
|---|---|
| 10: reactor | |
| 21: absorption tower | 22: air stripper tower |
| 23: solvent recovery tower | 24: high boiling removal tower |
| 25: solvent refining tower | 26: butadiene removal tower |
| 30: first stream | |

Description of Reference Numerals

| | |
|---|---|
| 40: second stream | |
| 50: third stream | |
| 60: quenching tower | 70: compressor |
| 90: turbine | 100: heat exchanger |

What is claimed is:

1. A method for recycling energy in a process of butadiene preparation using oxidative dehydrogenation reaction, the method comprising steps of:
   a) supplying a part or all of a light gas discharged from a solvent absorption tower to a turbine to produce electricity;
   b) passing the light gas passed through the turbine to one or more device units equipped with a heat exchanger; and
   c) circulating the light gas that has passed through the device unit equipped with the heat exchanger back into an oxidative dehydrogenation reactor,
   wherein a temperature of the light gas discharged from the turbine ranges from −50° C. to 20° C.

2. The method of claim 1, wherein a pressure of the light gas supplied to the turbine ranges from 5 to 20 KCG.

3. The method of claim 1, wherein a pressure of the light gas discharged from the turbine ranges from 1 to 5 KCG.

4. The method of claim 1, wherein a temperature of the light gas supplied to the turbine ranges from 5 to 50° C.

5. The method of claim 1, wherein a temperature of the light gas discharged from the turbine ranges from −50 to 0° C.

6. The method of claim 1, wherein the turbine provides electricity yield ranging from 1 to 200 kWh/BD ton.

7. The method of claim 1, wherein the heat exchanger is a multistage heat exchanger in which one or more same type of heat exchangers are connected in sequence.

8. The method of claim 1, wherein the device unit is selected from a heat exchanger and a solvent streamline equipped with a heat exchanger.

9. The method of claim 8, wherein the device unit is a heat exchanger, and produces a refrigerant ranging from −10 to 30° C. in temperature from the heat exchanger.

10. The method of claim 8, wherein the device unit is a solvent streamline equipped with a heat exchanger, and the temperature of a solvent stream in the solvent streamline ranges from 5 to 50° C.

* * * * *